US005582739A

United States Patent [19]

Kaiser et al.

[11] Patent Number: 5,582,739
[45] Date of Patent: Dec. 10, 1996

[54] REDUCTION OF THE PHOSPHATE CONTENT IN WASTE WATER FROM THE PREPARATION OF METAL SALTS OF ASCORBIC ACID 2-MONOPHOSPHATE

[75] Inventors: Klaus Kaiser, Neustadt; Joachim Paust, Neuhofen, both of Germany

[73] Assignee: BASF Aktiengesellschaft, Ludwigshafen, Germany

[21] Appl. No.: 126,881

[22] Filed: Sep. 27, 1993

[30] Foreign Application Priority Data

Oct. 1, 1992 [DE] Germany .............. 42 32 997.3

[51] Int. Cl.$^6$ ........................................ C02F 1/58
[52] U.S. Cl. ............... 210/721; 210/724; 210/726; 210/754; 210/756; 210/759; 210/906; 549/222
[58] Field of Search ................... 210/702, 721, 210/724, 726, 754, 756, 759, 906; 549/222

[56] References Cited

U.S. PATENT DOCUMENTS

| 3,361,528 | 1/1968 | Shen | 210/906 |
|---|---|---|---|
| 4,179,445 | 12/1979 | Sieb et al. | 260/340.9 |
| 4,399,037 | 8/1983 | Diskowski et al. | 210/721 |
| 4,689,154 | 8/1987 | Zimberg | 210/721 |
| 4,724,262 | 2/1988 | Shimbo et al. | 549/222 |
| 4,999,437 | 3/1991 | Dobler et al. | 549/222 |
| 5,110,951 | 5/1992 | Ishimura et al. | 549/222 |
| 5,118,817 | 6/1992 | Yoshida et al. | 549/222 |
| 5,149,829 | 9/1992 | Seib et al. | 549/222 |
| 5,202,445 | 4/1993 | Dobler et al. | 549/315 |

FOREIGN PATENT DOCUMENTS

| 3909198 | 9/1990 | European Pat. Off. . | |
|---|---|---|---|
| 426020 | 5/1991 | European Pat. Off. . | |
| 4000977 | 7/1991 | Germany . | |
| 4026787 | 2/1992 | Germany . | |
| 2031889 | 2/1990 | Japan | 210/721 |
| WO91/13895 | 9/1991 | WIPO . | |

Primary Examiner—Peter A. Hruskoci
Attorney, Agent, or Firm—Keil & Weinkauf

[57] ABSTRACT

A process for reducing the phosphate content in waste water from the preparation of salts of ascorbic acid 2-monophosphate comprises A. treating the waste water from the crystallization of the metal salts of ascorbic acid 2-monophosphate with an alkali metal or alkaline earth metal hypochlorite, chlorine or $H_2O_2$, and B. precipitating, at a pH of 9–12, the inorganic phosphate which has been produced from organically bound phosphorus and/or was present in the waste water, especially as calcium phosphate.

6 Claims, No Drawings

REDUCTION OF THE PHOSPHATE CONTENT IN WASTE WATER FROM THE PREPARATION OF METAL SALTS OF ASCORBIC ACID 2-MONOPHOSPHATE

The present invention relates to an advantageous process for reducing the phosphate content in the waste water from the preparation of metal salts of ascorbic acid 2-monophosphate.

L-Ascorbic acid is an essential part of a balanced diet for humans and for livestock. Unfortunately, vitamin C is the least stable vitamin in foodstuff. Ascorbic acid 2-monophosphate is, by contrast, a form of vitamin C which is stable to oxidation. It has, moreover, a general bioavailability because it can be cleaved by phosphatases in vivo and in vitro to ascorbic acid (this has been demonstrated, for example, in guinea-pigs, broilers, piglets, Rhesus monkeys and fish). Accordingly, there have been numerous attempts to develop an advantageous process for preparing salts of ascorbic acid 2-monophosphate. Examples which may be mentioned are the processes disclosed in U.S. Pat. Nos. 4,179,445, 4,724,262, EP-A 426,020, DE-A 39 09 198, DE-A 40 00 977, DE-A 40 26 787, U.S. Pat. No. 4,179,445 and WO-A 91/13 895. The processes essentially differ in the way in which the large amounts of inorganic salts derived from the phosphorylation with $POCl_3$ are removed, and the method of precipitating the ascorbic acid 2-monophosphate. Good results have been achieved with precipitation of the ascorbic acid 2-monophosphate as KMg salt (cf. DE-A 39 09 198, 40 00 977 and 40 26 787) or as calcium salt (cf. U.S. Pat. No. 4,179,445 and WO-A 91/13895).

The disadvantage in most of the processes is that the waste water after crystallization of the metal salts of the ascorbic acid 2-monophosphate (generally called waste water herein) still have too high a phosphate content, which may result in eutrophication of the water courses into which it is discharged. In the interests of reducing environmental pollution, it is therefore desirable to reduce greatly the phosphate content in the waste water.

The phosphorus in the waste water is predominantly in organically bound form, eg. as non-precipitated ascorbic acid 2-monophosphate, as. bis-2-ascorbyl monophosphate and as other organic byproducts. Thus, for example, the waste water from the precipitation of L-ascorbic acid 2-monophosphate as calcium salt contains about 0.15% phosphorus and about 0.35% carbon, which means about 1.5 kg of P in 1 tonne of waste water.

It is an object of the present invention to develop a process which permits the content of phosphate in waste water from the preparation of ascorbate 2-monophosphate to be reduced considerably in the most simple and low-cost manner.

We have found that this object is achieved by a process for reducing the phosphate content in the waste water from the preparation of salts of ascorbic acid 2-monophosphate, which comprises A) treating the waste water from the crystallization of the metal salts of ascorbic acid 2-monophosphate with an alkali metal or alkaline earth metal hypochlorite, chlorine or $H_2O_2$ to release the organically bound phosphorus, and B) precipitating, at a pH of from 9 to 12, the inorganic phosphate obtained in this way and/or present in the waste water.

The process according to the invention is particularly advantageous when the inorganic phosphate is precipitated as calcium phosphate in step B. In the case of waste water which still contains sufficient calcium ions after the precipitation of the ascorbate 2-monophosphate, this can take place simply by adjusting the pH to about 9–12 using an alkali metal or alkaline earth metal hydroxide. In the case of waste water which contains no calcium ions or only inadequate amounts, lime water is added, while maintaining a pH of about 9–12, to the waste water which has been treated with the hypochlorite, chlorine or $H_2O_2$.

Re A)

The treatment of the waste water with a hypochlorite, $H_2O_2$ or chlorine surprisingly leads to very rapid and complete decomposition of the organic phosphorus compounds, and the resulting inorganic phosphate can now be precipitated.

It is advantageous to use as hypochlorite an alkali metal hypochlorite, especially sodium hypochlorite, in the form of its aqueous solution containing about 12–14% active chlorine, which is available commercially at very low cost.

The alkali metal or alkaline earth metal hypochlorite is generally used in amounts of from 1 to 2, preferably from 1.5 to 1.8, mol per mol of phosphorus compounds present in the waste water.

The treatment, according to the invention, of the waste water with chlorine is carried out simply by passing chlorine into the waste water. The chlorine is also used for this purpose in amounts of about 1–2, preferably 1.5–1.8, mol per mol of phosphorus compounds present.

The reaction with $H_2O_2$ is carried out by adding aqueous $H_2O_2$ solution to the waste water, where appropriate after acidification with HCl to a pH of 2–3. $H_2O_2$ is used for this purpose in amounts of about 1–10 mol per mol of the phosphorus compounds present. The reaction with $H_2O_2$ takes longer, especially if the waste water is not acidified. In general, it suffices to stir for 1–5, preferably 2–4, hours.

The considerable advantage of this treatment with a hypochlorite for the reduction in the phosphorus content in the waste water is evident, for example, from comparison of Example 2a with Comparative Example 2b.

Re B)

The phosphate ions obtained by the hypochlorite, chlorine or $H_2O_2$ treatment of the waste water can subsequently be precipitated.

In the case of waste water from the preparation of calcium salts of ascorbic acid 2-monophosphate, it suffices for this purpose to adjust the treated waste water to a pH of 9–12 with an alkali metal or alkaline earth metal hydroxide.

In the case of waste water from the preparation of other metal salts of ascorbic acid 2-monophosphate, it is necessary after the chlorine, $H_2O_2$ or hypochlorite treatment to add to the waste water a salt of a metal whose phosphates are sparingly soluble in water. Calcium compounds, aluminum sulfate or iron(III) salts can be used for this. It is particularly advantageous to use calcium compounds for this, especially lime water (aqueous solution of $Ca(OH)_2$) which is available at low cost.

The metal salt is generally used in amounts of about 2–6, preferably 3–5, mol per mol of inorganic phosphate.

The process according to the invention can be used to reduce the phosphorus content in waste water from the preparation of metal salts of ascorbic acid 2-monophosphate in a simple and low-cost manner to levels below 0.01% by weight.

EXAMPLE 1

670 g of a waste water from the crystallization of the calcium salt of ascorbic acid 2-monophosphate, containing 0.23% C, 0.1%=670 mg P, 0.37% Ca, 5.3% K, 0.03% Mg and 5.5% Cl, were mixed with 26.8 g of a sodium hypochlorite solution (12.5% active chlorine), and the mixture was stirred at room temperature (RT) for 10 minutes (min). The pH of the solution was then adjusted to 12 by adding 50% strength aqueous KOH and, after stirring for 8 hours, the precipitated solid was removed by filtration. Drying resulted in 10.98 g of crystals containing 7.8% C, 5.3% P, 17.5% Ca, 12.7% K, 1.5% Mg and 10.5% Cl, and the 665 g of filtrate contained 0.11% C, <0.01%, ie. <66 mg, P, 0.07% Ca, 5.4% K, <0.01% Mg and 5.8% Cl.

The P content in the waste water was thus reduced from 0.1% to less than 0.01%.

EXAMPLE 2 a) Waste water treatment according to the invention 525 g of a waste water from the crystallization of L-ascorbic acid 2-monophosphate as calcium salt, containing 0.43% C, 0.17% P, 0.58% Ca, 7.5% K and 8.0% Cl, were mixed with 21 g of a sodium hypochlorite solution (12.5% active chlorine), and the mixture was stirred at RT for 15 min. The pH of the solution was then adjusted to 12 by adding 50% strength aqueous KOH and, after stirring for 8 hours, the precipitated solid was filtered off. 510 g of filtrate containing 0.09% C, <0.01% P, 0.04% Ca, 7.7% K and 7.6% Cl were obtained.

The P content in the waste water was thus reduced from 0.17% to less than 0.01%.

b) Comparative Example 525 g of the waste water described in Example 2 were, without previous treatment with sodium hypochlorite solution, adjusted to pH 12 with a 50% strength aqueous KOH. The precipitated solid was filtered off after stirring for 8 hours. 503 ml of filtrate which contained 0.2% C, 0.04% P, 0.29% Ca, 7.6% K and 7.4% Cl were obtained.

The P content in the waste water was thus reduced only from 0.17% to 0.04%.

EXAMPLE 3

500 g of a waste water from the preparation of calcium L-ascorbate 2-phosphate, containing 0.18% P, 0.41% C, 0.54% Ca, 7.3% Cl, 7.2% K and 0.06% Mg, were mixed with 40 g of a 30% strength aqueous $H_2O_2$ solution, and the mixture was stirred at RT for 4 hours. The pH was then adjusted to 12 by adding 50% strength aqueous KOH and, after stirring for 8 hours, the precipitated solid was filtered off. This resulted in 528 g of a filtrate which contained 0.02% P, 0.23% C, <0.01% Ca, 6.7% Cl, 8.2% K and <0.01% Mg.

EXAMPLES 4 AND 5 WITH COMPARATIVE EXAMPLES

In each case, 300 g of a waste water from the preparation of calcium L-ascorbate 2-monophosphate with the phosphorus content evident from the table were mixed with the amount evident from the table of an aqueous sodium hypochlorite solution and, after stirring at RT for 10 minutes, adjusted to the pH stated in the table with 18% strength lime water or 50% strength aqueous KOH, and, after stirring for 8 hours, the precipitated solid was removed by filtration and dried. The phosphorus content in the treated waste water is reported in the table in % by weight and in total weight of phosphorus.

TABLE

| Example | Waste water before treatment | | Adjustment of the pH with | NaOCl [g/mol] | pH | Waste water after treatment | |
|---|---|---|---|---|---|---|---|
| | Amount [g] | P content [% by wt./g/mol] | | | | Amount [g] | P content [% by wt/g] |
| 4a* | 300 | 0.17/0.5/0.016 | Ca(OH)$_2$ | 15/0.026 | 8 | 302 | 0.04/0.12 |
| 4b | 300 | 0.17/0.5/0.016 | Ca(OH)$_2$ | 15/0.026 | 10 | 282 | <0.01/<0.03 |
| 4c | 300 | 0.17/0.5/0.016 | Ca(OH)$_2$ | 15/0.026 | 12 | 298 | <0.01/<0.03 |
| 5a | 300 | 0.17/0.5/0.016 | Ca(OH)$_2$ | 15/0.026 | 12 | 310 | <0.01/<0.03 |
| 5b* | 300 | 0.17/0.5/0.016 | Ca(OH)$_2$ | — | 12 | 281 | 0.02/0.06 |
| 5c* | 300 | 0.17/0.5/0.016 | KOH | — | 12 | 278 | 0.11/0.3 |

*Comparative example
Comparison of Examples 4b, 4c and 5a with Comparative Examples 4a, 5b and 5c shows clearly that only under the conditions according to the invention is it possible to reduce the phosphorus content in the treated waste water to less than 0.01% by weight.

We claim:

1. A process for reducing the content of phosphorus compounds including organic phosphorus compounds in the waste water which results from crystallization of ascorbic acid 2-monophosphate as a metal salt, which comprises
   A. treating the waste water with an alkali metal or alkaline earth metal hypochlorite, chlorine or $H_2O_2$ in order to decompose the organic phosphorus compounds into inorganic phosphate
   and
   B. precipitating, at a pH of 9–12, the inorganic phosphate in the waste water and removing said precipitated inorganic phosphate.

2. A process as defined in claim 1, wherein the waste water is treated with sodium hypochlorite in step A.

3. A process as defined in claim 1, wherein the waste water is treated with about 1–2 mol of the alkali metal or alkaline earth metal hypochlorite or of chlorine per mol of phosphorus compound present in step A.

4. A process as defined in claim 1, wherein the inorganic phosphate is precipitated as calcium phosphate in step B.

5. A process as defined in claim 1, wherein the inorganic phosphate is precipitated as calcium phosphate by adding lime water in step B.

6. A process as defined in claim 1, wherein the inorganic phosphate is precipitated as calcium phosphate in step B from a waste water which still contains sufficient calcium ions by adjusting the pH to about 9–12 using an alkali metal or alkaline earth metal hydroxide.

* * * * *